United States Patent
Barthel et al.

[11] Patent Number: 5,921,917
[45] Date of Patent: Jul. 13, 1999

[54] HAND-HELD VIEWING SYSTEM WITH REMOVABLE SHEATH

[75] Inventors: Thomas C. Barthel, Becker; Mark F. Brown, Coon Rapids, both of Minn.; Alan H. Shikani, Baltimore, Md.

[73] Assignee: Clarus Medical Systems, Inc., Minneapolis, Minn.

[21] Appl. No.: 08/954,145

[22] Filed: Oct. 20, 1997

[51] Int. Cl.[6] ........................................ A61B 1/04
[52] U.S. Cl. .................. 600/120; 600/121; 600/114; 128/200.26
[58] Field of Search ............................. 600/120, 131, 600/114, 115, 116, 182, 190, 188, 194, 197, 121; 128/200.26, 911, 912, 207.14; 604/117, 164, 165, 166, 280, 281, 264

[56] References Cited

U.S. PATENT DOCUMENTS

| | | | |
|---|---|---|---|
| 3,677,262 | 7/1972 | Zukowski | 128/6 |
| 3,776,222 | 12/1973 | Smiddy | 128/6 |
| 4,126,127 | 11/1978 | May | 128/11 |
| 4,319,563 | 3/1982 | Kubota | 128/6 |
| 4,561,446 | 12/1985 | Hetz | 128/660 |
| 4,782,819 | 11/1988 | Adair | 128/6 |
| 4,798,193 | 1/1989 | Giesy et al. | 128/7 |
| 4,800,870 | 1/1989 | Reid, Jr. | 128/6 |
| 4,846,153 | 7/1989 | Berci | 128/6 |
| 4,869,238 | 9/1989 | Opie et al. | 128/6 |
| 4,946,442 | 8/1990 | Sanagi | 604/164 |
| 4,947,896 | 8/1990 | Bartlett | 128/11 |
| 4,982,729 | 1/1991 | Wu | 128/11 |
| 5,127,393 | 7/1992 | McFarlin et al. | 128/4 |
| 5,183,031 | 2/1993 | Rossoff | 128/6 |
| 5,329,940 | 7/1994 | Adair | 128/200.26 |
| 5,337,735 | 8/1994 | Salerno | 128/11 |
| 5,512,034 | 4/1996 | Finn et al. | 600/138 |
| 5,569,159 | 10/1996 | Anderson et al. | 600/114 |
| 5,607,386 | 3/1997 | Flam | 600/120 |
| 5,636,625 | 6/1997 | Miyagi et al. | 128/200.26 |
| 5,645,519 | 7/1997 | Lee et al. | 600/120 X |

*Primary Examiner*—Beverly M. Flanagan
*Attorney, Agent, or Firm*—Olson & Hierl, Ltd.

[57] ABSTRACT

A hand-held viewing system for use during medical procedures including endotracheal intubations or tracheostomies is disclosed. The viewing system includes an endoscope assembly having a fiber optic bundle for indirectly viewing the tracheal area of a patient into which the breathing tube is being inserted and a malleable sheath on the endoscope assembly for guiding the tube into place within the patient's trachea. The viewing system also incorporates an adapter stop which allows the endoscope assembly to be used with breathing tubes of varied lengths. A handle is included to which the endoscope assembly and a viewing means are removably connected.

56 Claims, 5 Drawing Sheets

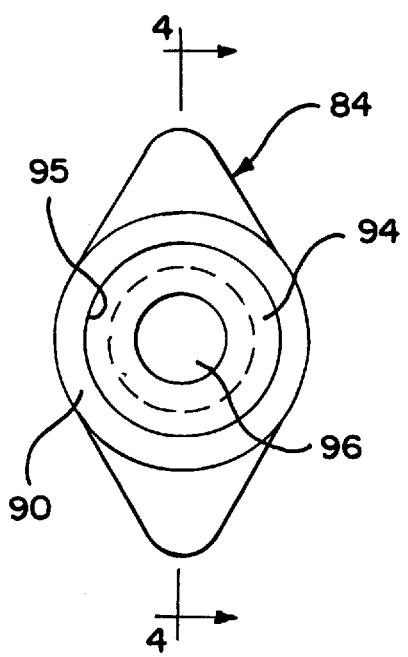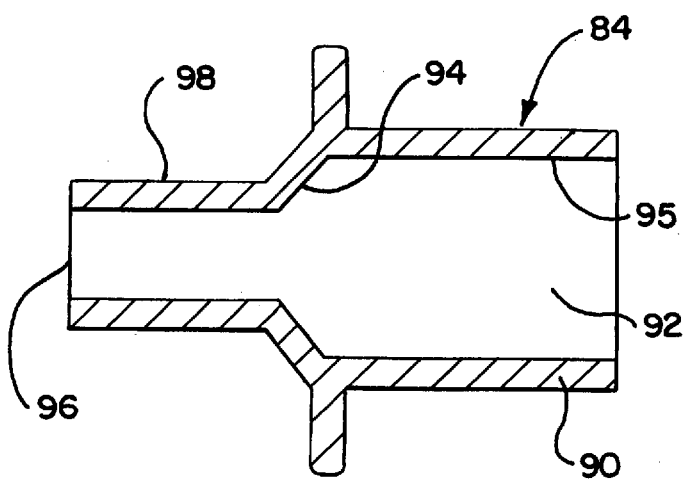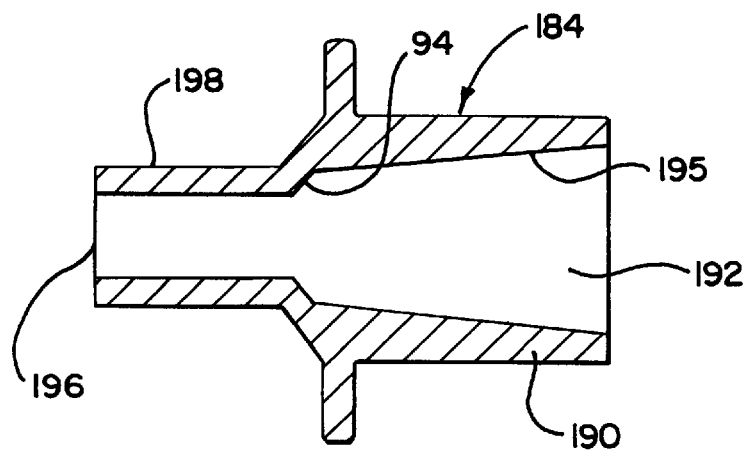

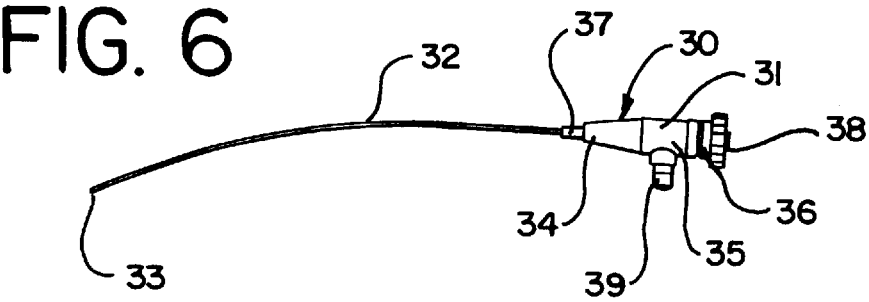
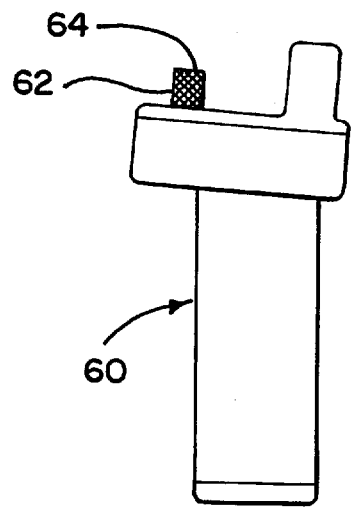
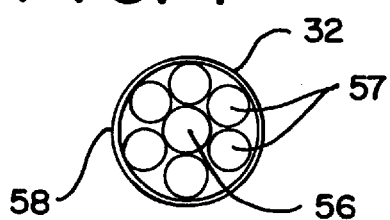
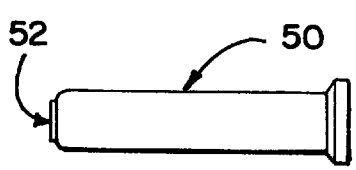
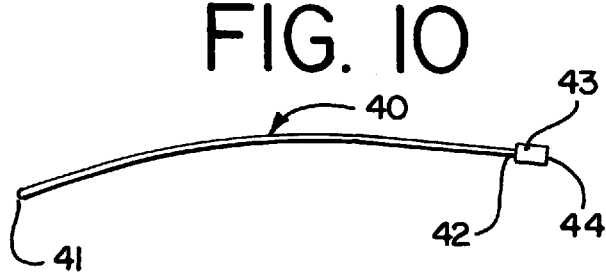
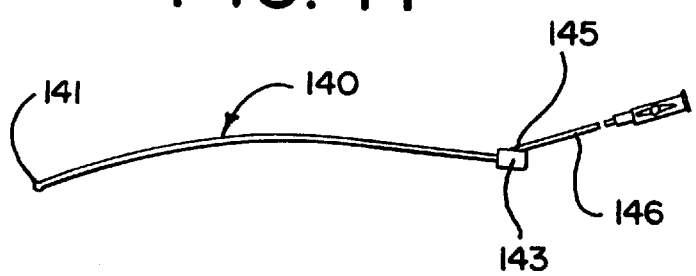
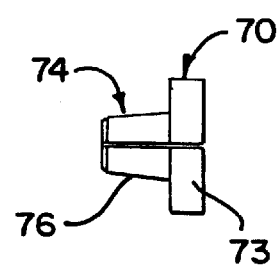

HAND-HELD VIEWING SYSTEM WITH REMOVABLE SHEATH

FIELD OF THE INVENTION

The present invention relates generally to a hand-held viewing system for assisting in endotracheal intubation or tracheostomy procedures or other endoscopic procedures.

BACKGROUND OF THE INVENTION

Endoscopes have been used in medical procedures for many years. Relatively recent developments in the field of fiber optics have allowed endoscopic devices to be developed for a wide range of medical applications. Also, advances in materials have resulted in devices that can be disposable and more economical.

In addition to procedures such as examinations of a patient, endoscopes have been employed to assist with procedures such as endotracheal intubation.

During an endotracheal intubation procedure, a flexible plastic endotracheal breathing tube is inserted into a patient's trachea for providing oxygen or anesthetic gases to the lungs. Usually, the endotracheal tube is introduced into the patient's trachea after the patient has been sedated or has become unconscious. Typically, the patient is placed on his or her back, and the patient's chin is lifted in order to place the patient in the so-called "sniffing" position. When the head and neck of the patient are situated to achieve the proper position, the patient's tongue typically falls downward toward the roof of the patient's mouth. The endotracheal tube must be inserted past the patient's teeth and tongue and further past the epiglottis and vocal cords into the trachea. After the endotracheal tube is advanced past the vocal cords and into the patient's trachea, the distal end of the tube should be approximately 2 to 4 centimeters (about 1 to 2 inches) in front of the bifurcation of the trachea in order to ventilate both of the patient's lungs equally.

Another procedure for providing oxygen or anesthetic gases to the lungs by placing a breathing tube into a patient's trachea is called a tracheostomy. Instead of inserting the breathing tube through the patient's mouth, an incision is made in the base of the patient's neck above the sternum so that a tracheostomy tube can be inserted into the patient's trachea.

Proper initial placement of a breathing tube is vital to the well-being of the patient. While breathing tubes are most often used for a relatively short period of time such as for surgery or under emergency conditions, sometimes a breathing tube is required by a patient for an extended period. In these cases it is desirable to change the patient's endotracheal or tracheostomy tube approximately weekly to prevent harmful reaction from long-term intubation such as granulation tissue reaction, infection, or stenosis of the trachea, larynx, or subglottis.

In some cases, the placement of the tube is made difficult due to trauma or physical differences in the tracheal areas of different patients. Also, patients differ in size, age, and sex. Serious complications may result if the tube is placed incorrectly, such as into the esophagus or into only one bronchus. With an endoscopic intubation assist device, the practitioner can view the patient's tracheal area and is able to more accurately place the tube. Existing devices, however, are not adjustable for different size patients that require various sizes of endotracheal or tracheostomy tubes.

In some cases, an elongated wire or stylet made of malleable material which can be bent or shaped to accommodate a particular patient is used to assist intubation. The malleable stylet is inserted into the endotracheal tube and then used to guide the tube into place within the patient's tracheal passage. The stylet is then removed, and the tube is connected to a supply conduit which then supplies the oxygen or other gas to the lungs of the patient. In the normal practice of endotracheal intubation procedures, the medical practitioner pre-shapes a 3 to 4 mm outside diameter aluminum stylet over which the endotracheal tube is placed and then follows a blind approach to accomplish intubation.

Fiber optics may be incorporated into the stylet which is used to guide the tube into place. Examples of intubation assist devices which incorporate fiber optics are disclosed in Adair, U.S. Pat. No. 5,329,940 entitled "Endotracheal Tube Intubation Assist Device;" Salerno, U.S. Pat. No. 5,337,735 entitled "Fiber-Lighted Stylet;" Berci, U.S. Pat. No. 4,846,153 entitled "Intubating Video Endoscope;" and Zukowski, U.S. Pat. No. 3,677,262 entitled "Surgical Instrument Illuminating Endotracheal Tube Inserter."

One disadvantage of these types of devices is that while they provide some viewing, they can be used with an endotracheal tube of only one length or a limited range of lengths within a particular category such as pediatric or adult. Also, many of these devices are relatively complicated in that they may include a suction port, oxygen or gas supplying means, gas flow directed means, or other control systems.

The prior art patents described all disclose fixed length endoscopes that can only be used with endotracheal tubes of only one length or of a limited range of lengths. These devices necessitate different versions for the many available endotracheal tubes from pediatric to adult sizes. Also, prior art devices that use fiber optics are relatively expensive and complex and therefore are not used very often because of the high cost of operating and maintaining these devices. The cost of repairing or replacing one of these units is very high compared to the that of the present invention.

A need exists in the art for an intubation assist device that allows the medical practitioner to view the tracheal area during the procedure. A hand-held viewing system with a construction that is easily assembled and disassembled is preferable. It would also be beneficial to be able to use one size of endoscopic viewing system with several sizes of endotracheal tubes such as from pediatric to adult sizes. The device also should be simple, inexpensive, and easy to use. The present invention meets these desires.

SUMMARY OF THE INVENTION

The present invention relates to a viewing system which can be used for several medical procedures including endotracheal intubation, tracheostomy, or other endoscopic procedures. The invention provides an image of the endotracheal area for use as a guide during an intubation procedure, for example.

The viewing system is comprised of an endoscope assembly that includes a mounting portion having a forward section with a first mating surface. The mounting portion also includes middle and rearward sections. The endoscope assembly also includes a flexible fiber optic bundle extending from the forward section and having a distal end. A first connector is preferably located on the rearward section of the mounting portion, and a second connector is preferably on the middle section.

In the preferred embodiment, a malleable sheath is mounted onto the endoscope assembly. The malleable sheath has a distal tip and a proximal end. The proximal end of the sheath preferably has a fitting for mounting the sheath onto the forward section of the endoscope assembly. The fitting has a second mating surface for frictionally engaging the first mating surface. When the sheath is mounted onto the endoscope assembly, the fiber optic bundle extends through the sheath and the distal tip of the sheath is preferably substantially coterminous with the distal end of the fiber optic bundle. The endoscope assembly provides the image via the fiber optic bundle within the malleable sheath.

A viewing means is releasably connected to one of the first connector and the second connector of the endoscope assembly, while an illumination source is releasably connected to the other of the first connector and the second connector. Preferably, the viewing means is releasably connected to the first connector and the illumination source is connected to the second connector.

Also in one preferred embodiment, a handle is provided that includes the illumination source and a support section for receiving and supporting the viewing means. The illumination source may include a light bulb and a battery, both enclosed within the handle. A receptacle is provided on the handle for connection to the second connector.

When the endoscope assembly and the viewing means are assembled, they can be further assembled to the handle. The endoscope assembly is removably mounted on the handle by the connection between the second connector and the receptacle, while the viewing means is removably mounted to the handle at the support section. The handle thus simultaneously cooperates with the endoscope assembly and the viewing means in a complimentary interengaging relationship. The receptacle and the support section of the handle are aligned and spaced apart so as to provide a stable structure supporting the endoscope assembly and viewing means at two places. An advantage of an assembly supported at the two places is that during use, twisting and rotation of the endoscope assembly in relation to the handle can be avoided. Another advantage of the viewing system of the present invention is the ease of assembly and disassembly.

When the endoscope assembly and the viewing means are mounted to the handle of this preferred embodiment, the malleable sheath of the present invention is removably mounted to the mounting portion of the endoscope assembly.

When the viewing system of the present invention is used for endotracheal intubation procedures, the preferred embodiment also may include an adapter stop for precisely locating the distal tip of the sheath as desired with respect to the distal end of the breathing tube so that the image of the tracheal area in front of the breathing tube can be provided. The advantage provided by the adapter stop of the present invention is that the sheath mounted on the endoscope assembly can be of a standard length and still be used with a breathing tube of any length.

When the endoscope assembly and breathing tube are successfully guided to the desired position within the trachea, the adapter stop is disengaged from the breathing tube, and the endoscope assembly can be removed while the tube is held in place. Oxygen or other gases can then be supplied to the patient.

While endotracheal and tracheostomy tubes are generally used only once, an advantage of the present invention is that the adapter stop, the malleable sheath, and the endoscope assembly can be reusable. Other advantages of the present invention are the relatively inexpensive and simple constructions of the adapter stop, the malleable sheath and the endoscope assembly compared to prior art devices.

In accordance with a method of the present invention, the viewing system is assembled by inserting the fiber optic bundle of the endoscope assembly into the malleable sheath. The sheath is then inserted through the adapter stop. The sheath is then inserted into the breathing tube. The practitioner then aligns the distal tip of the sheath of with respect to the distal end of the breathing tube. Once the sheath is aligned, the adapter stop with the endoscope assembly is mounted to the tube by mating the first and second mounting elements. In the preferred embodiment, the second mounting element of the adapter stop is inserted into the first mounting element of the breathing tube.

The adjustability provided by the adapter stop is advantageous, because the end of the fiber optic bundle can be placed substantially coterminously with the end of the breathing tube or at any other position desired. This is desirable, because the system will provide an image of the tracheal area from the point of view of the end of the breathing tube.

Numerous other advantages and features of the present invention will become readily apparent to those skilled in the art from the following detailed description of the preferred embodiment of the invention, the drawings, and the appended claims.

BRIEF DESCRIPTION OF THE DRAWINGS

FIG. 3 is a front elevational view of the first mounting element;

FIG. 4 is a cross-sectional view of the first mounting element taken along plane 4—4 of FIG. 3;

FIG. 5 is a cross-sectional view of an alternate embodiment of the first mounting element taken along plane 4—4 of FIG. 3;

FIG. 6 is a side elevational view of the endoscope assembly showing the fiber optic bundle and the mounting portion;

FIG. 7 is an end view of the fiber optic bundle of the endoscope assembly of FIG. 6;

FIG. 8 is a side elevational view of the handle;

FIG. 9 is a side elevational view of the viewing means;

FIG. 10 is a side elevational view of the sheath;

FIG. 11 is a side elevational view of an alternate embodiment of the sheath of FIG. 10;

FIG. 12 is a side elevational view of the adapter stop;

DETAILED DESCRIPTION OF THE PREFERRED EMBODIMENTS

Figure 1:
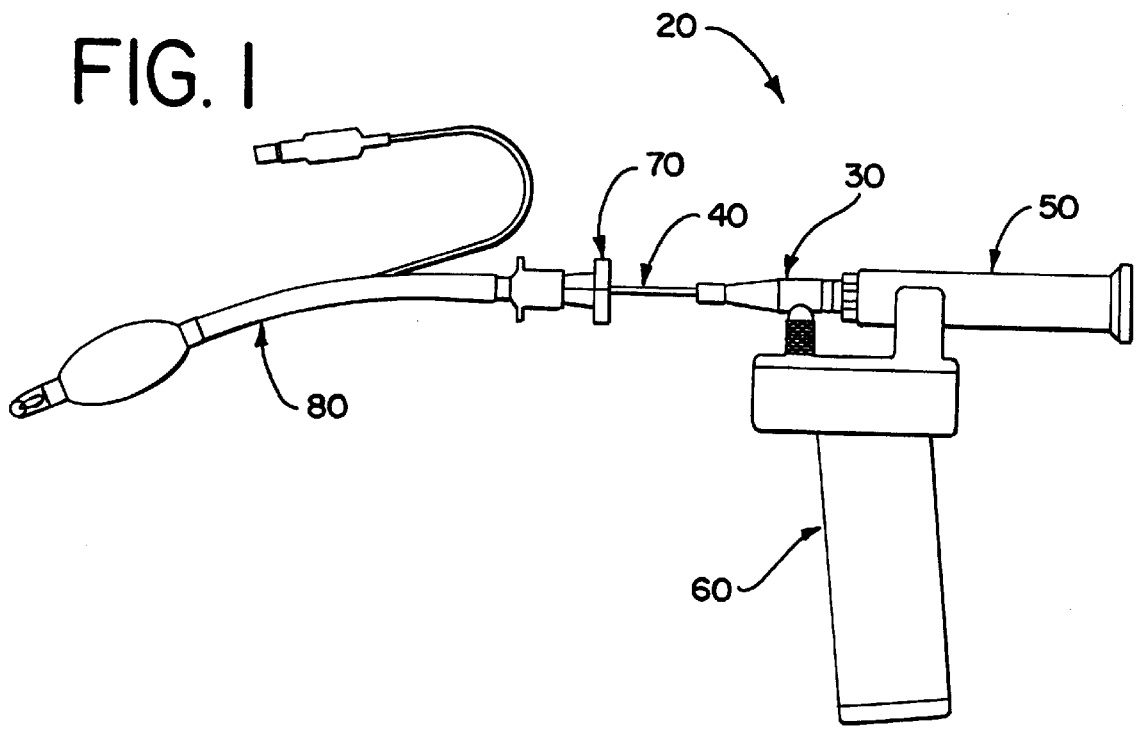
FIG. 1 is a plan view showing a viewing system of the present invention with an adapter stop, a malleable sheath, an endoscope assembly, and a viewing means mounted onto a handle, the viewing system being used with an endotracheal breathing tube.

While this invention can be embodied in many different forms, there are shown in the drawings and described in detail, preferred embodiments of the invention. The present disclosure is an exemplification of the principals of the invention and is not intended to limit the invention to the embodiments illustrated.

Figure 2:
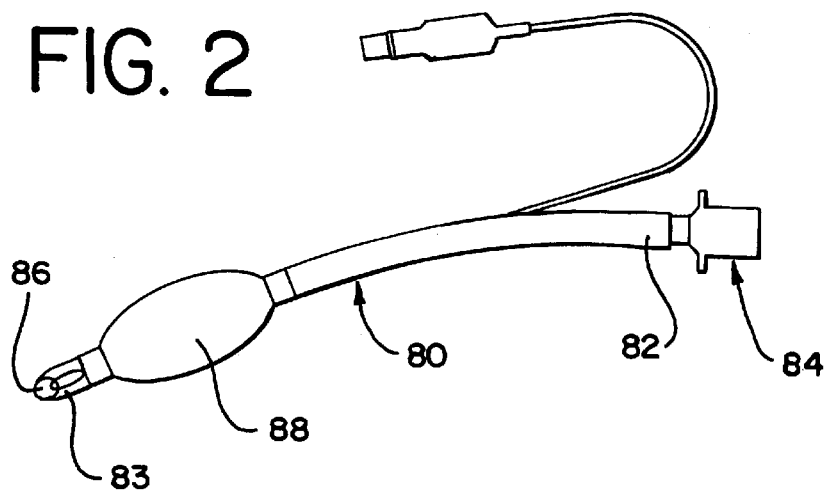
FIG. 2 is a side elevational view of the endotracheal tube.

Referring to FIG. 1 of the drawings, one embodiment of the present invention, a viewing system 20 with an endoscope assembly 30, a malleable sheath 40, a viewing means 50, a handle 60, and an adapter stop 70 is shown. The viewing system 20 can be used with a breathing tube such as an endotracheal tube 80, as shown in FIGS. 1 and 2.

The viewing system 20, comprising the endoscope assembly 30 and handle 60, when used for endotracheal intubation procedures has the advantage of providing an image of the tracheal area while inserting the endotracheal tube 80. This is a vast improvement over blind intubation. It is also a great improvement over the simple laryngoscope devices of the prior art which merely illuminate but do not provide an image of the tracheal area. Also, the adapter stop 70 provides an advantage over prior art devices which incorporate fiber-optics but do not allow the use of a standard length shaft 40 with endotracheal tubes 80 of varied lengths. FIG. 1 shows the viewing system of the present invention as embodiment in an easily assembled and disassembled system wherein all the parts have a complimentary interengaging relationship.

The present invention may be used with any endotracheal tube 80 that is commonly available. The common endotracheal tube 80, as shown in FIG. 2, has a proximal end 82, a distal end 83, and a first mounting element 84 on the proximal end 82, and is made of flexible plastic. The first mounting element 84 is commonly known as a "port" or "fitting." The first mounting element 84 is connected to a supply of oxygen or anesthetic gas during use. The first mounting element 84 is a standard size on all endotracheal and tracheostomy tubes, but the length of the tube may vary for different size patients such as pediatric or adult. While the breathing tube 80 is made of flexible plastic, the first mounting element 84 is typically made of a rigid plastic material and may be of the type commonly known as a "Luer fitting." The tube including the first mounting element 84 is sterile.

The endotracheal tube 80 also defines a lumen 86 between the ends 82 and 83. It is the distal end 83 of the endotracheal tube 80 that is inserted into the trachea of a patient. An inflatable cuff 88 is provided near the distal end 83 of the endotracheal tube 80. The cuff 88 is inflated after the tube 80 is in place within the trachea. Once inflated, the cuff 88 provides a seal between the tracheal wall and the endotracheal tube 80. The endotracheal tube 80 is open at both ends 82 and 83 to allow oxygen or anesthetic gas to flow through the tube 80 and into the patient's lungs once the tube 80 is inserted into the trachea and connected to an oxygen or gas supply.

As shown in FIGS. 3 and 4, the first mounting element 84 is comprised of a hollow cylinder 90 that defines a cavity 92 having a bottom surface 94 and a hole 96 that axially cooperates with the lumen 86 of the endotracheal tube 80 to join the cavity 92 and the lumen 86. The cavity 92 of the first mounting element 84 is usually defined by a substantially cylindrical inner surface 95. An alternate embodiment, shown in FIG. 5, provides the cavity 192 with a tapered inner surface 195 such that the taper becomes narrower toward the bottom surface 194 of the cavity 192.

The first mounting element 84 may be attached to the endotracheal tube 80 in any manner that provides a seal between the endotracheal tube 80 and the first mounting element 84. In the common configuration, the endotracheal tube 80 is slipped tightly over a tubular protrusion 98 that is opposite the cavity 92. The tubular protrusion 98 has an outer diameter dimensioned to be larger than the inner diameter of the endotracheal tube 80 so that the endotracheal tube 80 fits tightly over the protrusion 98.

Other possible configurations of the first mounting element 84 may include a threaded inner surface, a twist lock connector, or any type of connector that provides a positive locking mechanism for connecting the endotracheal tube 80 to an oxygen or anesthetic gas supply means. The adapter stop 70 is configured to cooperate with whatever configuration is used for the first mounting element 84.

Referring to FIG. 6, the endoscope assembly 30 of the preferred embodiment includes a mounting portion 31 and a fiber optic bundle 32.

The mounting portion of the endoscope assembly includes a first connector that can be connected to a viewing means such as an image viewing apparatus. The image viewing apparatus is preferably a video monitor, but it may be a mechanical lens or other device that allows the practitioner to view the image provided by the endoscope assembly. The fiber-optic bundle preferably includes optic fibers that carry illumination to the distal end of the bundle to illuminate the endotracheal area of the patient so that the practitioner can more easily see the area into which the breathing tube is being guided. The mounting portion can be molded around the proximal end 82 of the fiber optic bundle to secure the optic fibers in relation to the first and second connectors. Illumination may be provided by a light source within the handle attached to the endoscope assembly by the second connector.

The mounting portion 31 preferably includes a forward section 34, a middle section 35, and a rearward section 36. In accordance with this preferred embodiment, the forward section 34 includes a first mating surface 37, the rearward section 36 includes a first connector 38, and the middle section includes a second connector 39. Also, the fiber optic bundle 32 extends from the forward section 34.

As shown in FIG. 7, the fiber optic bundle 32 preferably contains at least one image-carrying optic fiber 56 for transmission of the image to the viewing means 50. The preferred embodiment of the fiber optic bundle 32 also includes at least one illumination-carrying optic fibers 57. One example of a configuration of the fiber of the fiber optic bundle 32 is the image-carrying fiber 56 disposed substantially in the center of the bundle with the illumination fibers 59 surrounding it as illustrated in FIG. 7. The bundle 32 of fibers is preferably flexible and encased in a flexible jacket 58 of thin-wall plastic.

Referring again to FIG. 6, the first mating surface 37 is preferably a substantially cylindrical protrusion extending from the forward section 34. The first mating surface 37 can alternatively be tapered slightly such that the taper is narrowest toward the fiber optic bundle 32 and widest toward the forward section 34.

One embodiment of the first connector 38 of the rearward section 36 is exemplified in FIG. 6 as a threaded locking ring type that can preferably be connected to the viewing means 50, shown in FIG. 9, via a mating connector. Alternatively, the viewing means 50 can be integral with the mounting portion 31.

The image-carrying fiber 56 is preferably located through the mounting portion 31 after it exits the fiber optic bundle 32, and is terminated adjacent to the first connector 38.

An embodiment of the second connector 39 is also illustrated in FIG. 6. In the preferred embodiment shown, the second connector 39 is a push-in type of connector which allows the endoscope assembly 30 to be mounted onto the handle 60 quickly and easily by snapping into a receptacle 62 on the handle 60. The illumination-carrying fibers 57 are preferably located through the mounting portion 31 after exiting the fiber optic bundle 32. In the preferred embodiment, the illumination carrying fibers 57 are disposed within the mounting portion 31 at approximately a right angle so as to terminate adjacent to the second connector 39.

In the preferred embodiment as shown in FIG. 6, the first and second connectors generally form a right angle. In an alternate embodiment, the first and second connectors can be at any angle that allows the endoscope assembly to be assembled to a viewing means and mounted on a handle.

When the endoscope assembly 30 and the viewing means 50 are mounted to the handle 60, the endoscope assembly 30 and the viewing means 50 are electrically insulated from the power source within the handle 60 (which can be a battery or ac). This insulation feature is advantageous because of increased safety to the patient.

Both the image-carrying fiber 56 and the illumination-carrying fibers 57 are located adjacent the respective connectors so as to be adjacent to the viewing means 50 and the illumination source 64.

In an alternate embodiment, the image-carrying fibers 56 can be located to be adjacent to the second connector 39, and the illumination-carrying fibers 57 can be located to be within the first connector 38.

The fiber optic bundle 32 of the preferred embodiment is at least one optic fiber and preferably is a bundle of 30,000 optic fibers. Multiple optic fibers may be used to provide better image resolution or to carry illumination in addition to carrying an image. For example, the fiber-optic bundle may be comprised of 30,000 fibers that are about 0.88 mm in diameter. Also, an image focusing device such as a lens may be associated with the fiber-optic bundle 32 at the distal end 83 of the bundle 32. Alternatively, the fiber optic bundle 32 can be any other suitable system which is flexible or bendable.

In use, the endoscope assembly 30 is in a cooperating interengaging relationship with the malleable sheath 40, as shown in FIG. 1.

FIG. 9 illustrates a preferred embodiment of the malleable sheath 40 of the present invention. The sheath 40 of the viewing system 20 is preferably malleable so that the practitioner can bend the sheath 40 into a desired shape for a particular patient. The malleable sheath 40 of this embodiment substantially retains the shape into which it is bent while the breathing tube is being inserted into the patient. This feature allows the viewing system 20 to be used with endotracheal tubes 80 of any length for different size patients when the viewing system is used for intubation. Since the sheath 40 may be shaped as desired, a single standard length sheath 40 may be used for any patient. Preferably, the length of the sheath 40 is approximately as long as the longest available endotracheal tube 80.

Yet another embodiment of the sheath 40 has an atraumatic tip of the type disclosed in U.S. Pat. No. 5,512,034. The bulbous tip prevents trauma to the patient should the sheath 40 of the viewing system 20 contact any internal tissue of the patient during the intubation procedure.

In the preferred embodiment as shown in FIGS. 1 and 10, the sheath 40 is tubular and malleable and the fiber optic bundle 32 is carried within the sheath 40.

In the preferred embodiment, the distal tip 41 is placed into the breathing tube and is generally aligned with the distal end of the tube. Preferably, the sheath is at least as long as the longest available endotracheal or tracheostomy tube. In the preferred embodiment, the sheath is malleable and is made of aluminum or preferably stainless steel tubing so that it can be bent or shaped to accommodate a particular patient's anatomy. The malleable sheath will substantially retain its shape in typical use once it is bent. In this preferred embodiment, the sheath is tubular so that the fiber optic bundle may extend through the sheath. This configuration results in a generally annular space between the endoscope and the sheath. The space allows irrigation or aspiration to be accomplished. The distal tip of the sheath is preferably open so that the distal end of the fiber optic bundle can provide illumination to the area into which the breathing tube is being inserted, and so that an image of this area can be transmitted back to the viewing means.

The proximal end 42 of sheath 40 has a fitting 43 for mounting the sheath onto the forward section 34 of the endoscope assembly 30. The fitting 43 is substantially cylindrical and defines a second mating surface 44 for frictionally engaging the first mating surface 37. Alternatively, the fitting 43 may define a locking or threaded mechanism for mounting onto the mounting portion 31.

Another alternative embodiment of the sheath 140 is illustrated in FIG. 11. This embodiment includes a port or opening 145 defined by the fitting 143 for aspiration or irrigation. An irrigation or aspiration tube 146 can be attached to the fitting 143 at the opening 145.

An example of the preferred embodiment of the viewing system is the Clarus Model 2127 laryngoscope. The sheath 40 is approximately 35 cm in length, about 2.5 to about 3.5 mm in diameter, and made of aluminum tubing about 0.5 mm thick or annealed stainless steel tubing with a wall thickness of about 0.3 mm.

When the sheath 40 is mounted to the endoscope assembly 30, the viewing system 20 can be used for an intubation procedure, for example. For intubation procedures, the adapter stop 70 is used.

Figure 13:
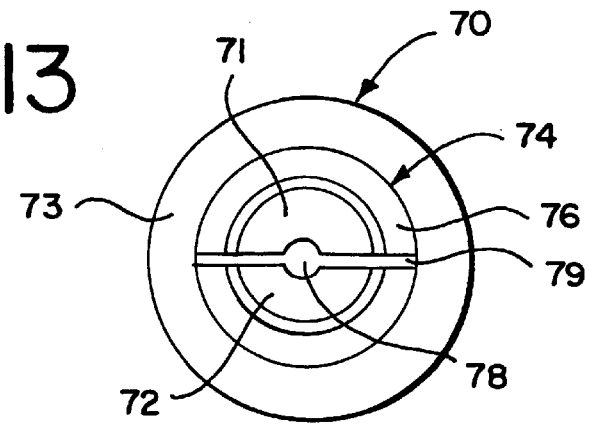
FIG. 13 is a front elevational view of the adapter stop of FIG. 12.

In the embodiment shown in FIGS. 12–13, the adapter stop 70 comprises a second mounting element 74 which is adapted to cooperate with the first mounting element 84 such that the adapter stop 70 receives and holds the sheath 40 in place within the lumen 86 of the endotracheal tube 80 when the first and second mounting elements are operably associated. The first and second mounting elements become operably associated when the second mounting element 74 is inserted into the cavity 92 of the first mounting element 84. The first mounting element 84 slips tightly over the second mounting element 74 while compressing the second mounting element 74 to hold the sheath.

The adapter stop is preferably a one-piece plastic construction that allows the practitioner to securely mount the breathing tube to the sheath which is mounted on the endoscope assembly. When mounted to the tube, the adapter stop compresses on the sheath to hold it in the desired position within the breathing tube. Once the distal tip of the sheath is located with respect to the distal end of the tube, the sheath is locked into place by inserting the second mounting element of the adapter stop into the first mounting element of the tube.

The second mounting element 74 comprises a locking section. The locking section 76 is dimensioned to mate within the cavity 92 of the first mounting element 84. The locking section 76 of the preferred embodiment has the shape of a tapered cylinder. The diameter of the tapered locking section 76 is dimensioned so that as the locking section 76 is pushed into the cavity 92 of the first mounting element 84, an interference fit is eventually produced between the first and second mounting elements when the locking section 76 is mounted within the cavity 92. The interference fit produces friction which holds the locking section 76 within the cavity 92 and also causes the locking section 76 to compress on the sheath 40 to hold it in place.

Once the adapter stop 70 and the endoscope assembly are mounted onto the endotracheal tube 80, the viewing system 20 can be used as a handle to physically maneuver the endotracheal tube 80 past the patient's teeth, tongue, epiglottis, and vocal cords into its proper position about 2 to 4 cm (about 1 to 2 inches) in front of the bifurcation of the trachea.

Figure 16:
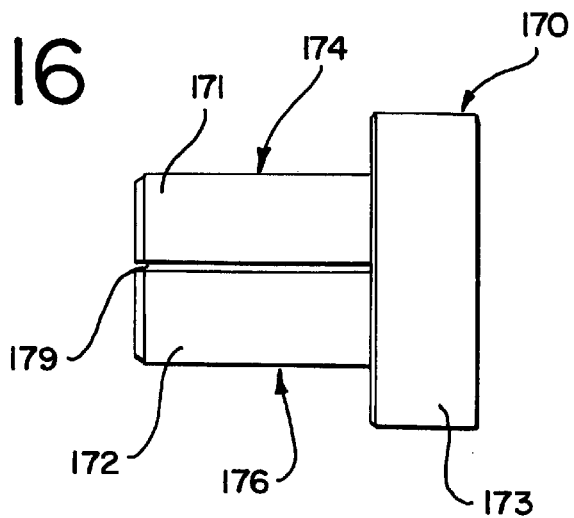
FIG. 16 is a side elevational view of an alternate embodiment of the adapter stop of FIG. 12.

In another embodiment, the locking section 176 is substantially cylindrical, as shown in FIG. 16, while the inner surface 195 defining the cavity 192 is tapered, as shown in FIG. 5. The same result of an interference fit will be obtained. Other possible embodiments of the locking section 76 may include non-cylindrically shaped locking sections and cavities, i.e., rectangular or triangular, or threaded or snap-fit locking sections which provide a positive mechanical connection between the first and second mounting elements.

In the preferred embodiment shown in FIGS. 12–13, the adapter stop 70 comprises the locking section 76 having two ends and defining a channel between the ends for movably receiving the sheath 40 when the adapter stop 70 is unmounted. Preferably, the adapter stop 70 holds the sheath 40 in place inside of the endotracheal tube 80 when the first and second mounting elements are operably associated. The channel is dimensioned to be larger in diameter than the sheath 40 so that the sheath 40 moves freely within the adapter stop 70 when the adapter stop 70 is not mounted within the cavity 92 of the first mounting element 84.

The sheath 40 gripping feature of the second mounting element 74 may be accomplished in the preferred embodiment by a longitudinal slot 79 defined by the locking section 76. The slot 79 extends radially from the channel 78 of the locking section and axially through the second mounting element 74. The slot separates the second mounting element 74 into a first half 71 and a second half 72. When the adapter stop 70 is mounted in the cavity 92, the first mounting element 84 compresses the locking section 76, thereby squeezing together the first and second halves of the locking section 76 which are separated by the slot. The squeezing together of the two halves cause the halves to compress on the sheath 40 which is in position within the channel of the adapter stop 70.

Figure 14:
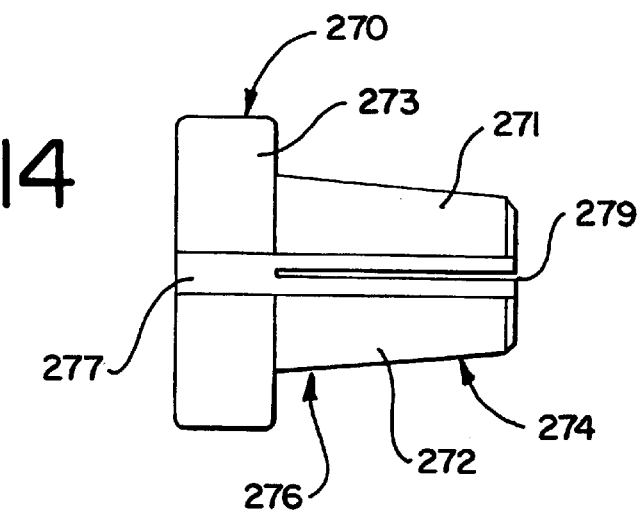
FIG. 14 is a side elevational view of an alternate embodiment of the adapter stop of FIG. 13.
Figure 15:
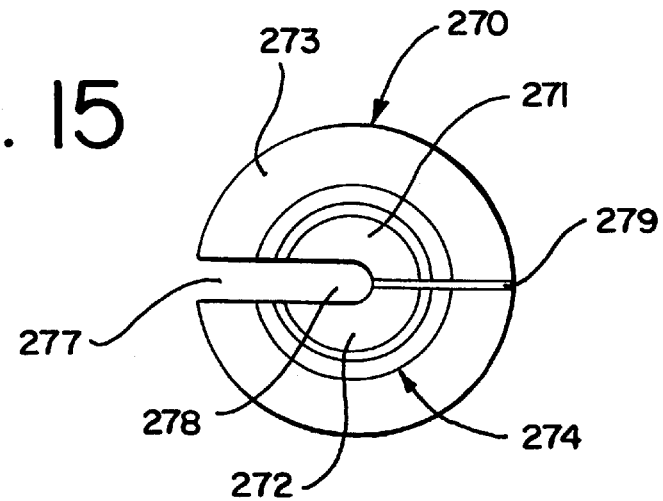
FIG. 15 is a front elevational view of the alternate embodiment of the adapter stop of FIG. 14.

FIGS. 14–15 show an alternate preferred embodiment of the adapter stop 170. This embodiment is similar to the embodiment shown in FIGS. 12–14 except that the locking section 276 and the second mounting element 274 define a substantially longitudinal shaft receiving slot for receiving the sheath 40. The slot 277 of this alternate embodiment extends radially from the axis of the elongated hollow body as is shown in FIGS. 14–15. The slot 277 is for laterally receiving the sheath 40 so that the adapter handle may be assembled to the endoscope assembly by aligning sheath 40 with the slot and inserting the sheath 40 into the adapter handle.

Additionally, the alternate embodiment of FIGS. 14–15 shows a clamping slot 279 defined by the second mounting element 74. The clamping slot 279 extends radially from the axis of the second mounting element 74 and extends axially through the second mounting element 74. The clamping slot and the shaft receiving slot are operably associated such that the second mounting element 74 grips and holds the sheath 40 in place within the lumen 86 of the endotracheal tube 80 via the same mechanism as the previously described preferred embodiment.

FIGS. 12–13 show another feature of the adapter stop which is a collar 73 extending radially from the second mounting element 74. In this preferred embodiment, the collar is disc shaped.

In use, the alternate preferred embodiments of the adapter stop 270, shown in FIGS. 14–15 accomplish the same result of gripping and holding the sheath 40 within the lumen 86 of the endotracheal tube 80 by receiving the sheath 40 laterally through the shaft receiving slots.

The adapter stop 70 preferably is made of sterilizable plastic and is a simple, inexpensive, one-piece construction. The adapter stop 70 can be made by any method of manufacture suitable for making plastic pieces including injection molding or machining.

In use, the practitioner assembles the viewing system 20 by inserting the sheath 40 into the adapter stop 70 and through the endotracheal tube 80. If the sheath 40 is malleable, it may first be shaped as desired or required for a particular patient. Alternatively, the sheath 40 may by shaped after the tube 80 is mounted onto the adapter stop 70.

Since endotracheal tubes 80 vary in length, the location of the endoscope assembly 30 with respect to the end of the endotracheal tube 80 should preferably be adjustable. The present invention allows the user to align the distal tip of the sheath 40 with respect to the distal end 83 of the tube 80, regardless of the length of the tube 80. Once the endoscope 30 assembly is aligned, the adapter stop 70 with the endoscope assembly 30 is mounted to the endotracheal tube 80 by mating the first and second mounting elements.

When mounted to the tube 80, the adapter stop 70 preferably compresses on the sheath 40 of the endoscope assembly 30 to hold it in the desired position within the endotracheal tube 80. The adjustability provided by the adapter stop 70 is advantageous, because the end of the sheath 40 of the endoscope assembly 30 can be placed substantially conterminously with the end of the endotracheal tube 80. This is desirable, because the viewing system 20 can provide an image of the tracheal area from the point of view of the end of the endotracheal tube 80.

After assembling the viewing system 20 and the endotracheal tube 80 and preparing the patient for intubation, the practitioner uses the image provided by the viewing system 20 as a guide to insert the endotracheal tube 80 into the trachea of the patient. The handle 60 may be used together with the sheath 40 to maneuver the endotracheal tube 80 into position.

When the endoscope assembly 30 and endotracheal tube 80 are successfully guided to the desired position within the trachea, the adapter stop 70 is disengaged from the endotracheal tube 80, and the endoscope assembly is removed while the tube 80 is held in place. The cuff 88 is then inflated and oxygen or other gases can be supplied to the patient.

Figure 17:
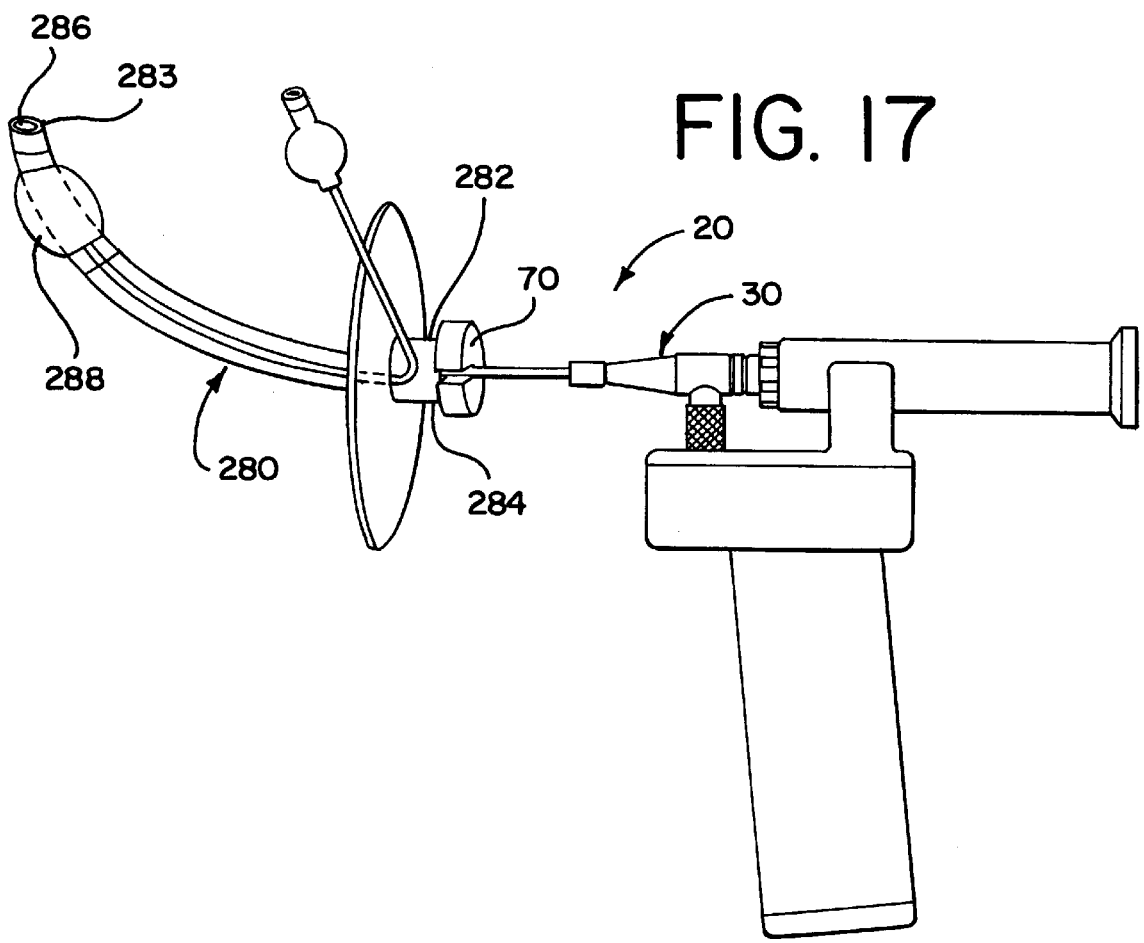
FIG. 17 is a plan view showing the viewing system and adapter stop mounted onto a tracheostomy tube.

As shown in FIG. 17, the adapter stop 70, or any of its alternate embodiments, may be used with the endoscope assembly 30 and a tracheostomy tube 280 in the same manner as with the endotracheal tube 80 as described herein. The tracheostomy tube is inserted into the patient via an incision at the base of the patient's neck above the sternum. The tracheostomy tube may have the same type of first mounting element 84 as the endotracheal tube 80. The tracheostomy tube also has a proximal end 282, a distal end 283, a lumen 286, and an inflatable cuff 288.

Although the invention has been described with reference to certain preferred embodiments, numerous modifications and variations can be made by those skilled in the art without departing from the novel spirit and scope of this invention.

What is claimed is:

1. A viewing system comprising:
   (a) an endoscope assembly including a mounting portion having a forward section with a first mating surface, a middle section, and a rearward section, the assembly also including a flexible fiber optic bundle extending from the forward section and having a distal end, a first connector on the rearward section, and a second connector on the middle section;
   (b) a malleable sheath having a distal tip, a proximal end, and a fitting at the proximal end for removably mounting the sheath onto the forward section of the endoscope assembly, the fitting having a second mating surface for engaging with the first mating surface of the forward section, the sheath being mounted onto the endoscope assembly with the fiber optic bundle extending through the sheath and the distal tip of the sheath being substantially coterminous with the distal end of the fiber optic bundle;
   (c) a viewing means connected to one of the first connector and second connector of the endoscope assembly; and
   (d) an illumination source connected to the other of the first connector and the second connector of the endoscope assembly.

2. The viewing system of claim 1 wherein the first mating surface is tapered.

3. The viewing system of claim 1 wherein the second mating surface is tapered.

4. The viewing system of claim 1 wherein the fiber optic bundle contains at least one image-carrying optic fiber for carrying an image from the distal end of the fiber optic bundle and at least one illumination-carrying optic fiber for carrying illumination from the illumination source to the distal end of the fiber optic bundle.

5. The viewing system of claim 4 wherein the viewing means includes at least one lens for direct ocular viewing of the image being carried from the distal end of the fiber optic bundle.

6. The viewing system of claim 4 wherein the viewing means includes a video system for viewing the image, the video system being connected to one of the first connector and the second connector of the endoscope assembly.

7. The viewing system of claim 1 wherein the illumination source is enclosed within a handle.

8. The viewing system of claim 7 wherein the handle defines a support section for receiving and supporting the viewing means.

9. The viewing system of claim 1 further including a breathing tube having a proximal end, a distal end, defining a lumen between the ends, and having a first mounting element on the proximal end.

10. The viewing system of claim 9 further including an adapter stop having a second mounting element adapted to cooperate with the first mounting element such that the adapter stop movably receives the malleable sheath when the first and second mounting elements are not associated and holds the sheath in place within the lumen of the breathing tube when the first and second mounting elements are operably associated.

11. A viewing system comprising:
    (a) an endoscope assembly including a mounting portion having a forward section with a first mating surface, a middle section, and a rearward section, the assembly also including a flexible fiber optic bundle extending from the forward section and having a distal end, a first connector on the rearward section, and a second connector on the middle section;
    (b) a malleable sheath having a distal tip, a proximal end, and a fitting at the proximal end for mounting the sheath onto the forward section of the endoscope assembly, the fitting having a second mating surface for frictionally engaging with the first mating surface of the forward section, the fitting defining an opening for injection of a fluid into the sheath, the sheath being mounted onto the endoscope assembly with the fiber optic bundle extending through the sheath and the distal tip of the sheath being substantially coterminous with the distal end of the fiber optic bundle;
    (c) a viewing means connected to one of the first connector and second connector of the endoscope assembly; and
    (d) an illumination source connected to the other of the first connector and the second connector of the endoscope assembly.

12. The viewing system of claim 11 further including a tube attached to the fitting at the opening.

13. A viewing system comprising:
    (a) an endoscope assembly including a mounting portion having a forward section with a first mating surface, a middle section, and a rearward section, the assembly also including a flexible fiber optic bundle extending from the forward section and having a distal end, a first connector on the rearward section, and a second connector on the middle section;
    (b) a malleable sheath having a distal tip, a proximal end, and a fitting at the proximal end for mounting the sheath onto the forward section of the endoscope assembly, the fitting having a second mating surface for frictionally engaging with the first mating surface of the forward section, the sheath being mounted onto the endoscope assembly with the fiber optic bundle extending through the sheath and the distal tip of the sheath being substantially coterminous with the distal end of the fiber optic bundle;
    (c) a viewing means connected to one of the first connector and second connector of the endoscope assembly;
    (d) an illumination source connected to the other of the first connector and the second connector of the endoscope assembly;
    (e) a breathing tube having a proximal end, a distal end, defining a lumen between the ends, and having a first mounting element on the proximal end; and
    (f) an adapter stop having a second mounting element adapted to cooperate with the first mounting element such that the adapter stop movably receives the malleable sheath when the first and second mounting elements are not associated and holds the sheath in place within the lumen of the breathing tube when the first and second mounting elements are operably associated, the adapter stop also having a locking section having two ends and defining an axial channel between the ends for movably receiving the malleable sheath when the adapter stop is unmounted and holding the malleable sheath in place inside of the breathing tube when the first and second mounting elements are operably associated.

14. The viewing system of claim 13 wherein the second mounting element is on one end of the locking section, and the first mounting element comprises a hollow cylinder having an inner surface defining a cavity dimensioned such that an interference fit is produced between the first and second mounting elements when the adapter stop is mounted within the cavity.

15. The viewing system of claim 14 wherein the second mounting element is tapered and the inner surface defining the cavity is substantially cylindrical.

16. The viewing system of claim 14 wherein the second mounting element is substantially cylindrical and the inner surface defining the cavity is tapered.

17. The viewing system of claim 13 wherein the locking section defines a substantially longitudinal slot having a predetermined width and extending radially from the channel and axially through the second mounting element such that the slot becomes narrower when the first mounting element cooperates with the second mounting element so that the shaft is held in place within the breathing tube.

18. The viewing system of claim 13 wherein the adapter stop further comprises a collar extending radially from the locking section and wherein the adapter stop defines an axis, a substantially longitudinal sheath-receiving slot extending radially from the axis and axially through the adapter stop, and a substantially longitudinal clamping slot extending radially from the axis and axially through the second mounting element, such that the clamping slot is operably associated with the sheath-receiving slot.

19. A viewing system comprising:
(a) a handle including an illumination source, a receptacle, and a support section;
(b) an endoscope assembly including a mounting portion having a forward section with a first mating surface and a flexible fiber optic bundle extending from the forward section and having a distal end, a first connector for connection to a viewing means, and a second connector for connection to the illumination source through the receptacle and for removably mounting the endoscope assembly onto the handle;
(c) a viewing means removably connected to the first connector of the endoscope assembly and removably mounted on the support section of the handle; and
(d) a malleable sheath having a distal tip, a proximal end, and a fitting at the proximal end for removably mounting the sheath onto the forward section of the endoscope assembly, the fitting having a second mating surface for engaging with the first mating surface of the forward section, the sheath being mounted onto the endoscope assembly.

20. The viewing system of claim 19 wherein the first mating surface is tapered.

21. The viewing system of claim 19 wherein the second mating surface is tapered.

22. The viewing system of claim 19 wherein the fiber optic bundle contains at least one image-carrying optic fiber for carrying an image from the distal end of the fiber optic bundle and at least one illumination-carrying optic fiber for carrying illumination from the illumination source to the distal end of the fiber optic bundle.

23. The viewing system of claim 22 wherein the viewing means includes at least one lens for direct ocular viewing of the image being carried from the distal end of the fiber optic bundle.

24. The viewing system of claim 22 wherein the viewing means includes a video system for viewing the image, the video system being connected to one of the first connector and the second connector of the endoscope assembly.

25. The viewing system of claim 19 further including a breathing tube having a proximal end, a distal end, defining a lumen between the ends, and having a first mounting element on the proximal end.

26. The viewing system of claim 25 further including an adapter stop having a second mounting element adapted to cooperate with the first mounting element such that the adapter stop movably receives the malleable sheath when the first and second mounting elements are not associated and holds the sheath in place within the lumen of the breathing tube when the first and second mounting elements are operably associated.

27. A viewing system comprising:
(a) a handle including an illumination source, a receptacle, and a support section;
(b) an endoscope assembly including a mounting portion having a forward section with a first mating surface and a flexible fiber optic bundle extending from the forward section and having a distal end, a first connector for connection to a viewing means, and a second connector for connection to the illumination source through the receptacle and for removably mounting the endoscope assembly onto the handle;
(c) a viewing means removably connected to the first connector of the endoscope assembly and removably mounted on the support section of the handle; and
(c) a malleable sheath having a distal tip, a proximal end, and a fitting at the proximal end for mounting the sheath onto the forward section of the endoscope assembly, the fitting having a second mating surface for frictionally engaging with the first mating surface of the forward section, the fitting defining an opening for injection of a fluid into the sheath, the sheath being mounted onto the endoscope assembly.

28. The viewing system of claim 27 further including a tube attached to the fitting at the opening.

29. A viewing system comprising:
(a) a handle including an illumination source, a receptacle, and a support section;
(b) an endoscope assembly including a mounting portion having a forward section with a first mating surface and a flexible fiber optic bundle extending from the forward section and having a distal end, a first connector for connection to a viewing means, and a second connector for connection to the illumination source through the receptacle and for removably mounting the endoscope assembly onto the handle;
(c) a viewing means removably connected to the first connector of the endoscope assembly and removably mounted on the support section of the handle;
(c) a malleable sheath having a distal tip, a proximal end, and a fitting at the proximal end for mounting the sheath onto the forward section of the endoscope assembly, the fitting having a second mating surface for frictionally engaging with the first mating surface of the forward section, the sheath being mounted onto the endoscope assembly;
(d) a breathing tube having a proximal end, a distal end, defining a lumen between the ends, and having a first mounting element on the proximal end; and
(e) an adapter stop having a second mounting element adapted to cooperate with the first mounting element such that the adapter stop movably receives the malleable sheath when the first and second mounting elements are not associated and holds the sheath in place within the lumen of the breathing tube when the first and second mounting elements are operably associated, the adapter stop also having a locking section having two ends and defining an axial channel between the ends for movably receiving the malleable sheath when the adapter stop is unmounted and holding the malleable sheath in place inside of the breathing tube when the first and second mounting elements are operably associated.

30. The viewing system of claim 29 wherein the second mounting element is on one end of the locking section, and the first mounting element comprises a hollow cylinder having an inner surface defining a cavity dimensioned such that an interference fit is produced between the first and second mounting elements when the adapter stop is mounted within the cavity.

31. The viewing system of claim 30 wherein the second mounting element is tapered and the inner surface defining the cavity is substantially cylindrical.

32. The viewing system of claim 30 wherein the second mounting element is substantially cylindrical and the inner surface defining the cavity is tapered.

33. The viewing system of claim 29 wherein the locking section defines a substantially longitudinal slot having a predetermined width and extending radially from the channel and axially through the second mounting element such that the slot becomes narrower when the first mounting element cooperates with the second mounting element so that the shaft is held in place within the breathing tube.

34. The viewing system of claim 29 wherein the adapter stop further comprises a collar extending radially from the locking section and wherein the adapter stop defines an axis, a substantially longitudinal sheath-receiving slot extending radially from the axis and axially through the adapter stop, and a substantially longitudinal clamping slot extending radially from the axis and axially through the second mounting element, such that the clamping slot is operably associated with the sheath-receiving slot.

35. A viewing system comprising:
(a) a handle including an illumination source, a receptacle, and a support section;
(b) an endoscope assembly including a mounting portion having a forward section with a tapered first mating surface, a middle section, and a rearward section, the assembly also including a flexible fiber optic bundle extending from the forward section and having a distal end, a first connector on the rearward section for connection to a viewing means, and a second connector on the middle section for connection to the illumination source and for mounting the endoscope assembly onto the handle;
(c) a viewing means connected to the first connector of the endoscope assembly and mounted to the support section of the handle; and
(d) a malleable sheath having a distal tip, a proximal end, and a fitting at the proximal end for removably mounting the sheath onto the forward section of the endoscope assembly, the fitting having a tapered second mating surface for engaging with the tapered first mating surface of the forward section, the sheath being mounted onto the endoscope assembly with the fiber optic bundle extending through the sheath and the distal tip of the sheath being substantially coterminous with the distal end of the fiber optic bundle;
(e) a breathing tube having a proximal end, a distal end, defining a lumen between the ends, and having a first mounting element on the proximal end; and
(f) an adapter stop having a second mounting element adapted to cooperate with the first mounting element such that the adapter stop movably receives the malleable sheath when the first and second mounting elements are not associated and holds the shaft in place within the lumen of the breathing tube when the first and second mounting elements are operably associated.

36. The viewing system of claim 35 wherein the fiber optic bundle contains at least one image-carrying optic fiber for carrying an image from the distal end of the fiber optic bundle and at least one illumination-carrying optic fiber for carrying illumination from the illumination source to the distal end of the fiber optic bundle.

37. The viewing system of claim 36 wherein the viewing means includes at least one lens for direct ocular viewing of the image being carried from the distal end of the fiber optic bundle.

38. The viewing system of claim 36 wherein the viewing means includes a video system for viewing the image, the video system being connected to one of the first connector and the second connector of the endoscope assembly.

39. A viewing system comprising:
(a) a handle including an illumination source, a receptacle, and a support section;
(b) an endoscope assembly including a mounting portion having a forward section with a tapered first mating surface, a middle section, and a rearward section, the assembly also including a flexible fiber optic bundle extending from the forward section and having a distal end, a first connector on the rearward section for connection to a viewing means, and a second connector on the middle section for connection to the illumination source and for mounting the endoscope assembly onto the handle;
(c) a viewing means connected to the first connector of the endoscope assembly and mounted to the support section of the handle; and
(d) a malleable sheath having a distal tip, a proximal end, and a fitting at the proximal end for mounting the sheath onto the forward section of the endoscope assembly, the fitting having a tapered second mating surface for frictionally engaging with the tapered first mating surface of the forward section, the fitting defining an opening for injection of a fluid into the sheath, the sheath being mounted onto the endoscope assembly with the fiber optic bundle extending through the sheath and the distal tip of the sheath being substantially coterminous with the distal end of the fiber optic bundle;
(e) a breathing tube having a proximal end, a distal end, defining a lumen between the ends, and having a first mounting element on the proximal end; and
(f) an adapter stop having a second mounting element adapted to cooperate with the first mounting element such that the adapter stop movably receives the malleable sheath when the first and second mounting elements are not associated and holds the shaft in place within the lumen of the breathing tube when the first and second mounting elements are operably associated.

40. The viewing system of claim 39 further including a tube attached to the fitting at the opening.

41. A viewing system comprising:
(a) a handle including an illumination source, a receptacle, and a support section;
(b) an endoscope assembly including a mounting portion having a forward section with a tapered first mating surface, a middle section, and a rearward section, the assembly also including a flexible fiber optic bundle extending from the forward section and having a distal end, a first connector on the rearward section for connection to a viewing means, and a second connector on the middle section for connection to the illumination source and for mounting the endoscope assembly onto the handle;

(c) a viewing means connected to the first connector of the endoscope assembly and mounted to the support section of the handle;

(d) a malleable sheath having a distal tip, a proximal end, and a fitting at the proximal end for mounting the sheath onto the forward section of the endoscope assembly, the fitting having a tapered second mating surface for frictionally engaging with the tapered first mating surface of the forward section, the sheath being mounted onto the endoscope assembly with the fiber optic bundle extending through the sheath and the distal tip of the sheath being substantially coterminous with the distal end of the fiber optic bundle;

(e) a breathing tube having a proximal end, a distal end, defining a lumen between the ends, and having a first mounting element on the proximal end; and (f) an adapter stop having a second mounting element adapted to cooperate with the first mounting element such that the adapter stop movably receives the malleable sheath when the first and second mounting elements are not associated and holds the shaft in place within the lumen of the breathing tube when the first and second mounting elements are operably associated, the adapter stop also having a locking section having two ends and defining an axial channel between the ends for movably receiving the malleable sheath when the adapter stop is unmounted and holding the malleable sheath in place inside of the breathing tube when the first and second mounting elements are operably associated.

42. The viewing system of claim 41 wherein the second mounting element is on one end of the locking section, and the first mounting element comprises a hollow cylinder having an inner surface defining a cavity dimensioned such that an interference fit is produced between the first and second mounting elements when the adapter stop is mounted within the cavity.

43. The viewing system of claim 42 wherein the second mounting element is tapered and the inner surface defining the cavity is substantially cylindrical.

44. The viewing system of claim 42 wherein the second mounting element is substantially cylindrical and the inner surface defining the cavity is tapered.

45. The viewing system of claim 41 wherein the locking section defines a substantially longitudinal slot having a predetermined width and extending radially from the channel and axially through the second mounting element such that the slot becomes narrower when the first mounting element cooperates with the second mounting element so that the shaft is held in place within the breathing tube.

46. The viewing system of claim 41 wherein the adapter stop further comprises a collar extending radially from the locking section and wherein the adapter stop defines an axis, a substantially longitudinal sheath-receiving slot extending radially from the axis and axially through the adapter stop, and a substantially longitudinal clamping slot extending radially from the axis and axially through the second mounting element, such that the clamping slot is operably associated with the sheath-receiving slot.

47. A viewing system adapted for use with a breathing tube having a proximal end, a distal end, defining a lumen between the ends, and having a first mounting element on the proximal end, the viewing system comprising:

(a) an endoscope assembly including a mounting portion having a forward section with a first mating surface, a middle section, and a rearward section, the assembly also including a flexible fiber optic bundle extending from the forward section and having a distal end, a first connector on the rearward section, and a second connector on the middle section;

(b) a malleable sheath having a distal tip, a proximal end, and a fitting at the proximal end for removably mounting the sheath onto the forward section of the endoscope assembly, the fitting having a second mating surface for engaging with the first mating surface of the forward section, the sheath being mounted onto the endoscope assembly with the fiber optic bundle extending through the sheath and the distal tip of the sheath being substantially coterminous with the distal end of the fiber optic bundle; and (c) an adapter stop having a second mounting element adapted to cooperate with the breathing tube first mounting element such that the adapter stop movably receives the malleable sheath when the breathing tube first mounting element and the second mounting element are not associated and holds the sheath in place within the lumen of the breathing tube when the breathing tube first mounting element and the second mounting element are operably associated.

48. The viewing system of claim 47 wherein the first mating surface is tapered.

49. The viewing system of claim 47 wherein the second mating surface is tapered.

50. The viewing system of claim 47 wherein the fiber optic bundle contains at least one image-carrying optic fiber for carrying an image from the distal end of the fiber optic bundle and at least one illumination-carrying optic fiber for carrying illumination from the illumination source to the distal end of the fiber optic bundle.

51. The viewing system of claim 47 wherein the adapter stop further comprises a locking section having two ends and defining an axial channel between the ends for movably receiving the malleable sheath when the adapter stop is unmounted and holding the malleable sheath in place inside of the breathing tube when the breathing tube first mounting element and the second mounting element are operably associated.

52. The viewing system of claim 51 wherein the second mounting element is on one end of the locking section, and the breathing tube first mounting element comprises a hollow cylinder having an inner surface defining a cavity dimensioned such that an interference fit is produced between the breathing tube first mounting element and the second mounting element when the adapter stop is mounted within the cavity.

53. The viewing system of claim 52 wherein the second mounting element is tapered and the inner surface defining the cavity is substantially cylindrical.

54. The viewing system of claim 52 wherein the second mounting element is substantially cylindrical and the inner surface defining the cavity is tapered.

55. The viewing system of claim 51 wherein the locking section defines a substantially longitudinal slot having a predetermined width and extending radially from the channel and axially through the second mounting element such that the slot becomes narrower when the breathing tube first mounting element cooperates with the second mounting element so that the shaft is held in place within the breathing tube.

56. The viewing system of claim 51 wherein the adapter stop further comprises a collar extending radially from the locking section and wherein the adapter stop defines an axis, a substantially longitudinal sheath-receiving slot extending radially from the axis and axially through the adapter stop, and a substantially longitudinal clamping slot extending radially from the axis and axially through the second mounting element, such that the clamping slot is operably associated with the sheath-receiving slot.

* * * * *